United States Patent [19]

Kuroki et al.

[11] Patent Number: 5,234,593
[45] Date of Patent: Aug. 10, 1993

[54] FILTER FOR PURIFICATION OF PLATELETS

[75] Inventors: Hitoshi Kuroki; Shinichiro Kuroda, both of Ashigarakami, Japan

[73] Assignee: Terumo Kabushiki Kaisha, Tokyo, Japan

[21] Appl. No.: 581,923

[22] Filed: Sep. 13, 1990

[30] Foreign Application Priority Data

Sep. 18, 1989 [JP] Japan .................. 1-240221
May 23, 1990 [JP] Japan .................. 2-131242

[51] Int. Cl.$^5$ ............................. B01D 39/00
[52] U.S. Cl. ................ 210/496; 210/510.1; 422/101
[58] Field of Search .......... 210/446, 496, 510.1; 422/101; 604/4, 5, 6

[56] References Cited

U.S. PATENT DOCUMENTS

| | | | |
|---|---|---|---|
| 3,747,769 | 7/1973 | Brumfield | 210/350 |
| 3,768,653 | 10/1973 | Brumfield | 210/436 |
| 4,246,107 | 1/1981 | Takenaka et al. | 210/806 |
| 4,283,289 | 8/1981 | Meyst et al. | 210/448 |
| 4,330,410 | 5/1982 | Takenaka et al. | 210/767 |
| 4,416,777 | 11/1983 | Kuroda et al. | 210/446 |
| 4,453,927 | 6/1984 | Sinko | 604/5 |
| 4,642,089 | 2/1987 | Zupkas et al. | 210/458 |
| 4,701,267 | 10/1987 | Watanabe et al. | 210/806 |
| 4,737,139 | 4/1988 | Zupkas et al. | 210/458 |
| 4,743,371 | 5/1988 | Servas et al. | 210/342 |
| 4,933,291 | 6/1990 | Daiss et al. | 422/101 |
| 4,985,153 | 1/1991 | Kuroda et al. | 210/496 |

FOREIGN PATENT DOCUMENTS

| | | |
|---|---|---|
| 0313348 | 4/1989 | European Pat. Off. . |
| 0331174 | 9/1989 | European Pat. Off. . |
| 61-39060 | 9/1986 | Japan . |
| 63-26089 | 5/1988 | Japan . |
| WO89/02304 | 3/1989 | PCT Int'l Appl. . |
| WO89/02305 | 3/1989 | PCT Int'l Appl. . |

Primary Examiner—Robert A. Dawson
Assistant Examiner—Sun Uk Kim
Attorney, Agent, or Firm—Burns, Doane, Swecker & Mathis

[57] ABSTRACT

A filter for the purification of platelets by dint of selective removal of leucocytes as extraneous matter from blood components, which filter has as a main part thereof a porous body possessing a three-dimensional reticularly continuous texture containing continuous open pores 6 to 12 μm in average diameter and allowing substantially no presence of acute projection inside said pores.

5 Claims, 2 Drawing Sheets

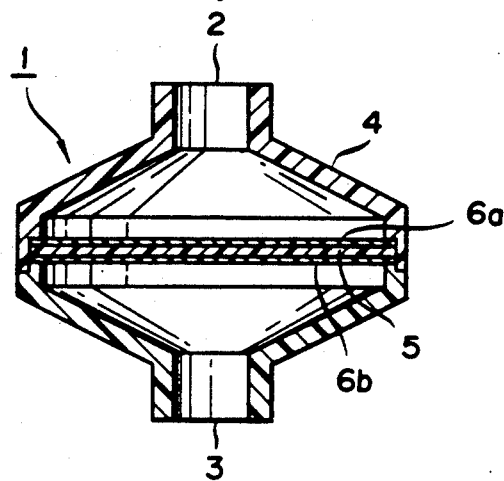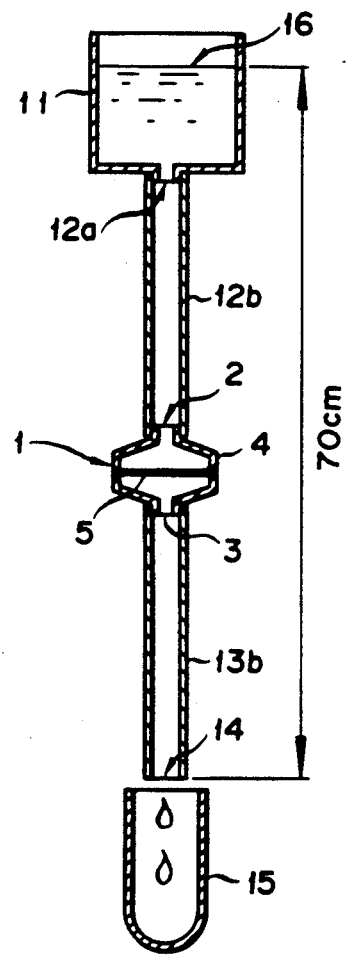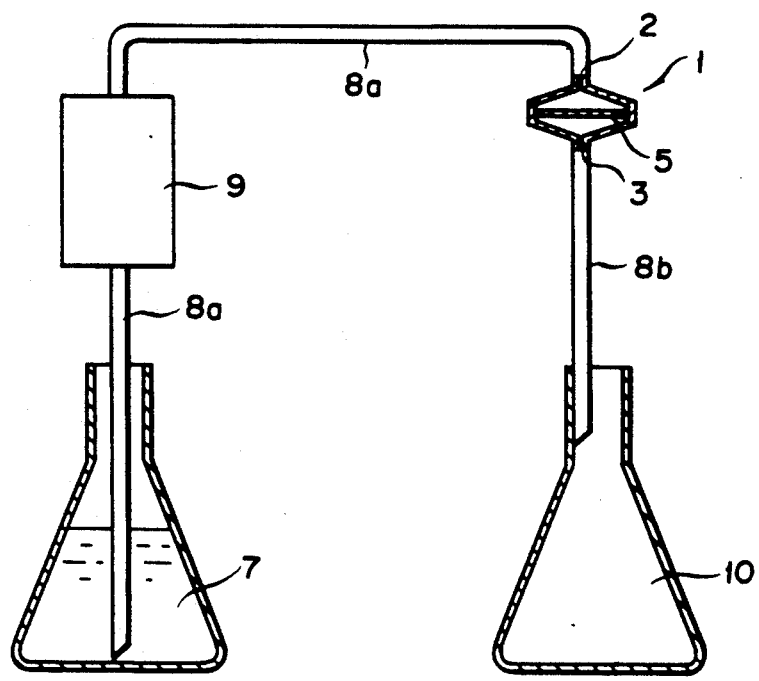

FILTER FOR PURIFICATION OF PLATELETS

BACKGROUND OF THE INVENTION

1. Field of the Invention

This invention relates to a filter for the purification of platelets. More particularly, it relates to a filter through which is passed a platelet suspension thereby effecting selective removal of leucocytes as extraneous matter therefrom and consequent separation of platelets in a purified form.

2. Description of the Prior Art

Today, the form of blood transfusion is increasingly tending from the whole blood transfusion toward the component blood transfusion using only the blood component required for a given patient. The number of kinds of medicines using platelets is increasing year after year. In recent years, the transfusion of platelets has been steadily gaining in importance in proportion to continuous increase of patients of thrombocytopania caused by heavy dosage of chemotherapeutic agents used against malignant tumors.

The platelet medicines actually put to use to date include the bag PC (platelet concentrate) prepared after collection of blood in a bag and the apheresis PC obtained by the use of a component blood collecting device. They both require separation of platelets from blood by the method of centrifugal separation.

The current method of centrifugal separation, however, inevitably suffers leakage of leucocytes (mainly lymphocytes) into the PC. It has been found that the leucocytes in the PC induce fever and other similar secondary effects after the transfusion of platelets and most patients taking frequent transfusion of platelets acquire refractoriness to the effect of transfusion. These adverse effects are logically explained by a supposition that the leucocytes give rise to human leucocyte antigen (HLA) and lymphocytetoxic antigen (LCT) in the patients' body.

The platelet transfusion is required to be performed frequently in large doses. The patient is consequently affected by many and unspecified antigens. It is said that the LCT antigen is detected in not less than 90% of the patients taking transfusion of 100 units or more of platelet medicine. When platelets are transfused into patients who have already developed such antibodies, the transfusion manifests the expected effect because the platelets are prone to destruction in the patients' bodies.

Various types of filters have been developed for the removal of leucocytes and have been already introduced to the market. They are either formed by having various kinds of fibers such as natural fibers like natural cellulose, synthetic fibers of polyesters, polyamides, and polyacrylonitrile, and inorganic fibers like glass fibers simply packed in their unmodified form in columns or provided with a filter part of secondarily fabricated non-woven fabric. They are chiefly intended to remove leucocytes mingling into such an erythrocyte medicine as the CRC (concentrated red corpuscles). Though these filters for the removal of leucocytes manifest their performance above a certain level concerning the removal of leucocytes, they are not prevented from removing platelets at the same time. They bring about an improper effect, therefore, when they are used for the removal of leucocytes from a platelet suspension or from whole blood.

In the circumstances, a desire has been expressed for a method or apparatus for permitting transfusion of pure platelets by removal of leucocytes, particularly lymphocytes, from such blood components as platelet suspensions and whole blood which contains leucocytes and platelets.

An object of the present invention, therefore, is to provide a novel filter for the purification of platelets.

Another object of this invention is to provide a filter for the purification of platelets, which filter is capable of selectively removing leucocytes a extraneous matter from such blood components as platelet suspensions and whole blood which contain leucocytes and platelets.

SUMMARY OF THE INVENTION

The objects described above are accomplished by a filter for the purification of platelets through the selective removal of leucocytes as extraneous matter from blood components, which filter has as a main part thereof a porous body possessing a three-dimensional reticularly continuous texture containing continuous open pores 6 to 12 μm in average diameter, and allowing substantially no presence of acute projections inside the pores.

This invention further discloses a filter for the purification of platelets, wherein the porous body is formed of polyurethane resin. This invention further discloses a filter for the purification of platelets, wherein the pore diameters are distributed in the range of 2 to 30 μm.

This invention is directed to a filter which is constructed as described above to permit purification of platelets. This filter, therefore, has a distinct and stable ability to seize leucocytes. Since this film possesses a porous structure such as to avoid inducing viscosity relative to leucocytes, it is capable of effecting highly efficient separation of leucocytes as extraneous matter from the platelet suspension such as the platelet concentrate or from whole blood and consequently accomplishing purification of the platelet suspension or the whole blood. Use of the purified platelet suspension or the purified whole blood is expected to allow effective prevention of the induction of fever and other similar side effects after the transfusion of platelets and the development of refractoriness to the effect of transfusion. Further, since the film has as a main part thereof a porous body of a three-dimensional reticularly continuous texture, it can be very easily sealed in a container such as a housing and can be very conveniently manufactured. The filter has no possibility of falling off its container and leaving behind a gap for leakage of extraneous matter. In the filter of this invention, when the porous body is formed of polyurethane resin and the pores therein have a diameter distribution in the range of 2 to 30 μm, the ratio of removal of leucocytes and the ratio of recovery of platelets are further improved.

BRIEF DESCRIPTION OF THE DRAWINGS

FIG. 1 is a schematic cross section illustrating a filter for the purification of platelets as one embodiment of this invention, FIG. 2 and FIG. 3 are schematic diagrams illustrating blood treating apparatuses each incorporating therein a filter for the purification of platelets as one embodiment of this invention.

EXPLANATION OF THE PREFERRED EMBODIMENT

Figure 4:
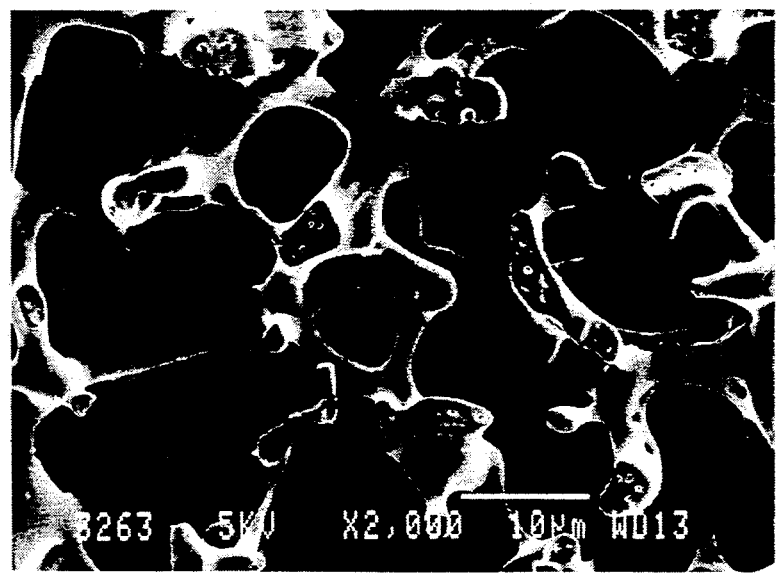
FIG. 4 is a photomicrograph illustrating the structure of a filter to be used in the present invention.

For selective removal of leucocytes mingling as extraneous matter in a platelet suspension, it is necessary to seize leucocytes of low viscosity and avoid seizing platelets of high viscosity. The filter of the present invention for the purification of platelets is characterized by having as a main part thereof a porous body possessing a three-dimensional reticularly continuous texture containing continuous open pores 6 to 12 $\mu$m in average diameter and allowing substantially no presence of acute projections inside the pores. When this filter is used for treating blood components such as a platelet suspension and whole blood which contain both leucocytes and platelets, the leucocytes contained as extraneous matter in the blood components are efficiently seized while they are flowing through complicated paths of continuous open pores having diameters in the aforementioned fixed range and formed in the matrix of the porous body. In the meantime, the platelets are completely passed through the filter without being seized in the paths because the paths are the continuous open pores formed in the matrix of the porous body, because the paths preclude the presence of a three-dimensional structure such as to induce high viscosity relative to the platelets unlike the conventional filter for the removal of platelets which uses an intertwined mass of fine fibers as a filter material, and further because the continuous open pores have diameters amply large as compared with the diameters of platelets. Thus, the purification of platelets can be attained with high efficiency.

Further, since the flow paths of the filter are continuous open pores formed in the matrix of the porous body and they are formed while the porous body is taking shape finally during the course of its production, the process employed in the production of the filter for purification of platelets by the use of this porous body is very simple and the possible dispersion of quality among a lot of products is very small. Moreover, the matrix of the porous body possesses a continuous texture, the inner walls of the continuous open pores allow substantially no presence of acute projections, and the film surfaces formed by cutting the porous body have no projections of any kind. The filter, therefore, enjoys stability of quality and substantial freedom from the problem of exudation of foreign matter through the porous body or channeling of the flow paths while the filter is in service.

Now, the present invention will be described more specifically below with reference to the following embodiments:

The filter of the present invention for the purification of platelets has as a main part thereof a porous body possessing a three-dimensional reticularly continuous texture containing continuous open pores and allowing substantially no presence of acute projections inside the pores. It is preferred that the filter surfaces have the same structure as the filter interior or are flat and smooth.

In the porous body of the present invention which is constructed as described above, the continuous open pores preferably have an average pore diameter in the range of 6 to 12 $\mu$m, preferably 8 to 10 $\mu$m. If the average pore diameter is less than 6 $\mu$m, there arises the possibility that the platelets will be seized on account of their size and the leucocytes will be seized substantially wholly in the surface layer parts of the porous body and consequently the filter will incur the problem of clogging. Conversely, if the average pore diameter exceeds 12 $\mu$m, the ability of the filter to seize leucocytes owing to differences in size will be degraded.

If the porous body has an unduly small pore diameter distribution, it has the possibility of inducing the phenomenon of clogging because the leucocytes are substantially wholly seized in the surface layer parts of the porous body. The pore diameter distribution, therefore, preferably falls in the range of 2 to 30 $\mu$m, more preferably 5 to 20 $\mu$m. When the porous body has pores of suitable size and distribution as described above, the leucocytes mingling as extraneous matter in the blood components flowing through the porous body are seized in the surface layer parts or the inner part of the porous body or are caused to adhere to the inner part of the porous body in which the flow is suffered to stagnate.

The term "average pore diameter" as used in the present specification refers to the magnitude determined by the mercury injection method on the percentage scale in which 0% stands for a pore diameter resulting in perfect absence of injected mercury in all of the pores of the porous body and 100% for a pore diameter resulting in presence of injected mercury in all of the pores of the porous body and 50% for a pore diameter intermediate between the two pore diameters mentioned above, namely the "average pore diameter" contemplated by the present invention. Specifically, the average pore diameter has a significance in this invention such that when various particles are passed through the filter of the porous body, particles of diameters exceeding the average diameter of the pores in the porous filter are not easily passed through the filter. The term does not necessarily mean that particles of diameters exceeding the average pore diameter are never passed through the filter under any condition.

The term "pore diameter distribution" as used in the present specification refers to the pore diameters corresponding to the range of 10 to 90% of volumetric change of injected mercury during the determination by the mercury injection method. The term has significance in that pore diameters deviating from the pore diameter distribution are not completely absent but are present in a small proportion.

The porosity of the porous body, though variable with such factors as average pore diameter, is preferably approximately in the range of 30 to 95%, preferably 75 to 95%. If the porosity is less than 30%, there arises the possibility that the operation of the filter for the purification of platelets will require an extended time. Conversely, if the porosity exceeds 95%, there is the possibility that the filter will suffer from insufficient strength.

The thickness of the porous body, though variable with factors such as average pore diameter, porosity, and microstructure of the three-dimensional, reticularly continuous texture of the matrix, is preferably approximately in the range of 0.3 to 10.0 mm, preferably 0.5 to 3 mm. If the thickness of the porous body is less than 0.3 mm, there arises the possibility that the filter will fail to seize leucocytes. Conversely, if the thickness of the porous body exceeds 10.0 mm, there ensues the possibility that the filtration layer will have a depth so large as to add appreciably to the time required for the operation of the filter.

The present invention does not particularly discriminate the porous body on account of the material used so long as the porous body possesses the required structure. The material nevertheless is required to be such that it will neither allow ready adhesion thereto of platelets nor cause ready infliction of damage to blood corpuscles. The materials which are usable herein include polyurethane, polytetrafluoroethylene, polypropylene, and polycarbonates, for example. The synthetic resin foam of polyurethane, for example, or the porous body of synthetic resin having the surface thereof coated with such a material as segmented polyurethane which defies ready adhesion of blood corpuscles prove to be preferable.

FIG. 1 is a cross section illustrating a filter for the purification of platelets as one embodiment of the present invention. In the present embodiment, a filter 1 comprises a housing 4 provided with a blood component inlet 2 and a blood component outlet 3 and a porous body 5 endowed with such a structure as described above and laid across the empty space inside the housing 4. In the filter 1 for the purification of platelets constructed as described above, the porous body 5 may be optionally provided in the front and rear parts thereof with liquid-permeable supporting members 6a, 6b adapted to pinch the porous body 5 and keep it fast in place so that the porous body may be retained stably inside the housing 4.

The filter 1 for the purification of platelets is usable in an apparatus constructed as illustrated in FIG. 2. In the apparatus illustrated in FIG. 2, a liquid guide tube 8a that extends from inside a container 7 holding a leucocyte-containing PRP (platelet rich plasma) under treatment is laid through the medium of a suction pump 9 and is connected to the platelet suspension inlet 2 of the filter 1 for the purification of platelets, and a liquid guide tube 8b that is connected to the platelet suspension outlet 3 of the filter 1 extends into a platelet suspension recovery container 10. The operation of this apparatus for the purification of platelets is effected by actuating the suction pump 9 thereby leading the leucocyte-containing PRP out of the container 7, advancing it through the platelet suspension inlet 2 into the filter 1 for the purification of platelets, and allowing it to flow through the paths formed of continuous open pores of the porous body 5 inside the filter 1. The PRP which has been divested of leucocytes owing to the seizure by the porous body 5 and which has completed its travel through the porous body 5 is led through the suspension outlet 3 to the outside of the filter 1 where it is recovered inside the platelet suspension recovery container 10.

Where a blood component of high platelet concentration is to be produced from whole blood by the removal of leucocytes, the filter 1 is formed by having the porous body 5 fixed inside the housing 4 provided with the blood inlet 2 and the blood outlet 3 as illustrated in FIG. 3. Also, tubes 12b, 13b made of polyvinyl chloride can be connected to the blood inlet 2 and the blood outlet 3 of the filter 1. One of the tubes 12b interconnects the blood inlet 2 of the filter 1 with the blood outlet 12a of a blood container while the other tube 12b extends from the blood outlet 3 of the filter 1 and terminates in an open end 14. A blood recovery container 15 can be disposed under the open end 14 of the tube 13b. The two tubes 12b, 13b can have lengths that are substantially equal. held in the blood container 11 is at a distance of 70 cm from the open end 14 of the tube 13b. This head of 70 cm is utilized in causing flow of 50 ml of blood.

Now, the present invention will be described more specifically below with reference to working examples.

EXAMPLE 1

A disk 1 mm in thickness and 25 mm in diameter was punched out of a porous body of polycarbonate type polyurethane resin (produced by Toyo Polymer K.K.) possessing a texture illustrated in FIG. 4 containing pores of an average of 10 μm and allowing substantially no of acute projections inside the pores. This disk was incorporated in a filter assembly (available area 2.4 cm²) formed as illustrated in FIG. 1 to complete a filter 1 for the purification of platelets. This filter 1 was installed in an apparatus constructed as illustrated in FIG. 2.

A lymphocyte-containing PRP (number of platelets $3.5 \times 10^5$ to $5.5 \times 10^5/\mu l$ and number of leucocytes $3.5 \times 10^3$ to $4.5 \times 10^3/\mu l$) was prepared by suspending in the PRP collected from CPD-added fresh blood of a healthy man autolymphocytes separated by the density gradient centrifugal method.

In an apparatus constructed as illustrated in FIG. 2, the lymphocyte-containing PRP was fed at a flow rate of 1 ml/mm.cm² to the filter 1 (1 ml/min.cm² of the filter surface). The number of leucocytes and the number of platelets of the lymphocyte-containing PRP before and after passage through the filter were calculated by the use of a blood corpuscle calculating device (produced by Orthodiagnostic System Corp. and marketed under the product code of "ELT-8") The ratio of removal of leucocytes and the ratio of recovery of platelets were found in accordance with the following formulas.

Ratio of removal of leucocytes (%) = [1 − (Number of leucocytes after passage/number of leucocytes before passage)] × 100

Ratio of recovery of platelets (%) = (Number of platelets after passage/number of platelets before passage) × 100

The results are shown in Table 1.

EXAMPLE 2

A disk 1 mm in thickness and 47 mm in diameter was punched out of a porous body of polycarbonate type polyurethane resin (produced by Toyo Polymer K.K.) similar to that of Example 1 and incorporated in a filter assembly formed as illustrated in FIG. 1 to complete a filter 1 for the purification of platelets. This filter 1 was installed in an apparatus constructed as illustrated in FIG. 3.

In the apparatus constructed as illustrated in FIG. 3, 50 ml of a CPD-added blood of a normal man was fed at a head of 70 cm. The number of leucocytes and the number of platelets of the blood were calculated by the use of a blood corpuscle calculating device by Orthodiagnostic System Corp. and marketed under product code "ELT-u"). The ratio of removal of leucocytes and the ratio of recovery of platelets were found in the same manner as in Example 1. The results are shown in Table 1.

Control 1

Figure 5:
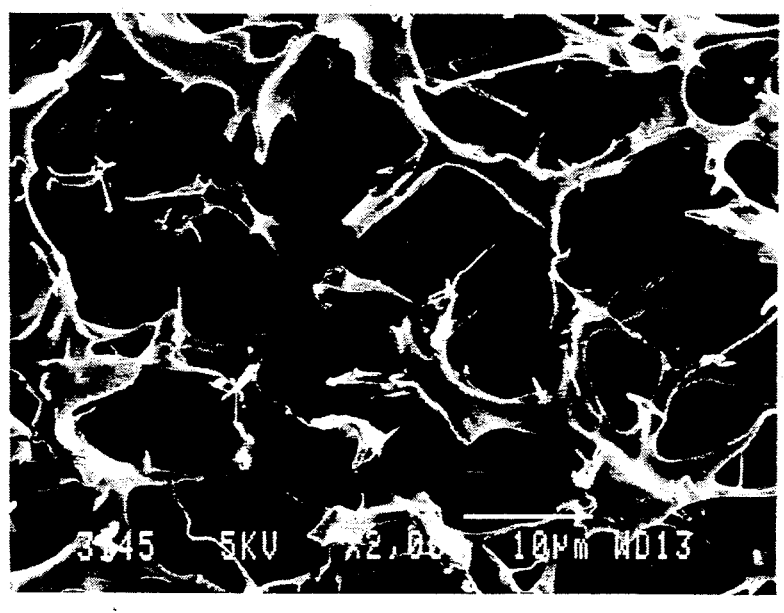
FIG. 5 is a photomicrograph illustrating the structure of a filter used for the purpose of comparison.

An experiment similar to that of Example 1 was carried out by the use of a body of continuous structure of polyvinyl formal resin (produced by Kanebo Ltd.) The body possessed the surface structure illustrated in FIG. 5, contained pores of an average diameter of 10 μm, contained of numerous acute projections inside the pores and also included thornlike projections on the filter surface. The experiment was performed to find the ratio of removal of leucocytes and the ratio of recovery of platelets. The results are shown in Table 1.

Control 2

An experiment similar to that of Example 2 was performed by the use of a body of continuous structure of polyvinyl formal resin similar to that of Control 1, to find the ratio of removal of leucocytes and the ratio of recovery of platelets. The results are shown in Table 1.

TABLE 1

|  | Ratio of removal of leucocytes (%) | Ratio of recovery of platelets (%) |
| --- | --- | --- |
| Example 1 | 100 | 95 |
| Example 2 | 100 | 72 |
| Control 1 | 100 | 60 |
| Control 2 | 100 | 35 |

EXAMPLES 3 TO 6 AND CONTROLS 3 AND 4

A disk 1 mm in thickness and 25 mm in diameter was punched out from a porous body of polycarbonate type polyurethane resin (produced by Toyo Polymer K.K.) possessing a structure similar to that illustrated in FIG. 4 and containing pores of varying average pore diameter and varying pore diameter distribution indicated in Table 2 and allowing substantially no presence of acute projections inside the pores. The disk was incorporated in a filter assembly formed as in FIG. 1 (available area 2.4 cm$^2$) to complete a filter 1 for the purification of platelets. This filter 1 was installed in an apparatus constructed as illustrated in FIG. 2.

A lymphocyte-containing PRP (number of platelets 3.5×10$^5$ to 5.5×10$^5$ /μl and number of leucocytes 3.5×10$^3$ to 4.5×10$^3$/μl) was prepared by suspending autolymphocytes separated by the density gradient centrifugal method in the PRP collected from a CPD-added fresh blood from a healthy man.

In an apparatus constructed as illustrated in FIG. 2, the lymphocyte-containing PRP was fed to the filter 1 at a flow rate of 1 ml/min.cm$^2$ (1 ml/min per cm$^2$ of the filter 1). The concentration of leucocytes and the concentration of platelets of the PRP before and after the passage through the filter 1 were calculated by the use of a blood corpuscle calculating device (produced by Orthodiagnostic Systems Corp. and marketed under product code of "ELT-8"). Then the absolute numbers of these blood corpuscle components were found based on the amounts of PRP and the ratio of removal of leucocytes and the ratio of recovery of platelets were found consequently. The results are shown in Table 2.

TABLE 2

|  | Control 3 | Example 3 | Example 4 | Example 5 | Example 6 | Control 4 |
| --- | --- | --- | --- | --- | --- | --- |
| Average pore diameter (μm) | 5 | 6 | 8 | 9 | 11 | 14 |
| Pore diameter distribution (μm) | 3~14 | 2~19 | 4~22 | 5~20 | 7~30 | 8~39 |
| Proportion of pore diameters distributed (%) |  |  |  |  |  |  |
| 30 μm~ | 2 | 4 | 6 | 4 | 9 | 15 |
| 25~30 μm | 1 | 1 | 2 | 2 | 4 | 5 |
| 20~25 μm | 1 | 3 | 3 | 3 | 8 | 9 |
| 18~20 μm | 3 | 2 | 3 | 4 | 4 | 4 |
| 16~18 μm | 1 | 3 | 4 | 3 | 5 | 5 |
| 14~16 μm | 2 | 4 | 6 | 6 | 8 | 10 |
| 12~14 μm | 2 | 5 | 7 | 4 | 9 | 17 |
| 10~12 μm | 3 | 9 | 6 | 4 | 23 | 16 |
| 8~10 μm | 5 | 9 | 10 | 35 | 19 | 9 |
| 6~8 μm | 15 | 9 | 25 | 22 | 6 | 5 |
| 4~6 μm | 33 | 17 | 15 | 9 | 3 | 4 |
| 2~4 μm | 26 | 27 | 10 | 3 | 1 | 1 |
| ~2 μm | 5 | 7 | 3 | 1 | 1 | 0 |
| Ration of removal of leukocytes (%) | 100 | 100 | 100 | 100 | 75 | 55 |
| Ratio of recovery of platelet (%) | 60 | 80 | 90 | 95 | 95 | 95 |

We claim:

1. A filter for the purification of platelets by dint of selective removal of leucocytes as extraneous matter from blood components, which filter includes a porous body possessing a three-dimensional reticularly continuous texture containing continuous open pores having an average diameter in the range of 6 to 12 μm, an average pore diameter distribution in the range of 2 μm to 30 μm and substantially no acute projections inside said pores, said average diameter being determined by a mercury injection method and being defined as the diameter of the pores at which the percentage of pores having a presence of injected mercury becomes 50%, assuming the percentage of pores into which mercury is injected is 100%.

2. A filter according to claim 1, wherein said average pore diameter is in the range of 8 to 10 μm.

3. A filter according to claim 1, wherein said porous body is formed of polyurethane resin.

4. A filter according to claim 3, wherein the thickness of said filter is in the range of 0.3 to 10.0 mm.

5. A filter according to claim 3, wherein the thickness of said filter is in the range of 0.5 to 3 mm.

* * * * *

UNITED STATES PATENT AND TRADEMARK OFFICE
CERTIFICATE OF CORRECTION

PATENT NO. : 5,234,593
DATED : August 10, 1993
INVENTOR(S) : Hitoshi KUROKI et al It is certified that error appears in the above-indentified patent and that said Letters Patent is hereby corrected as shown below:

In Column 2, line 9, delete "a" and insert -- as --.
In Column 5, line 49, before "suspension", insert -- platelet --.
In Column 5, line 62, delete "12b" and insert -- 13b --.
In Column 5, line 67, before "held", insert -- The level of the blood --.
In Column 6, line 12, delete "of".
In Column 6, line 58, before "by", insert -- (produced --.

Signed and Sealed this

Eighth Day of March, 1994

Attest:

BRUCE LEHMAN

Attesting Officer    Commissioner of Patents and Trademarks